United States Patent [19]

Kageyama

[11] Patent Number: 5,100,374

[45] Date of Patent: Mar. 31, 1992

[54] APPARATUS FOR DRIVING BLOOD PUMP

[75] Inventor: Toshinobu Kageyama, Okazaki, Japan

[73] Assignee: Aisin Seiki Kabushiki Kaisha, Tokyo, Japan

[21] Appl. No.: 468,881

[22] Filed: Jan. 23, 1990

[30] Foreign Application Priority Data

Jan. 31, 1989 [JP] Japan .................. 1-23442

[51] Int. Cl.$^5$ ............................................. A61M 1/10
[52] U.S. Cl. ....................................... 600/17; 600/16; 623/3
[58] Field of Search .................................. 600/16 ƒ 18; 623/3; 128/691

[56] References Cited

U.S. PATENT DOCUMENTS 4,546,760 10/1985 Suzuki et al. ..................... 600/16
4,662,355  5/1987 Pieronne et al. ................... 600/17
4,778,445 10/1988 Hubbard et al. ................... 128/691

FOREIGN PATENT DOCUMENTS

2153016 8/1985 United Kingdom ................. 600/17

Primary Examiner—Kyle L. Howell
Assistant Examiner—Kennedy J. Schaetzle
Attorney, Agent, or Firm—Burns, Doane, Swecker & Mathis

[57] ABSTRACT

An apparatus for driving a blood pump such as an artificial heart. The apparatus comprises a first pressure pulse generator, a second pressure pulse generator, a pressure detector for detecting the pressure produced by the first pressure pulse generator, a flow sensor for detecting the flow rate of blood passing through the pump, a selector device, and an electrical control unit. Normally, the first pressure generator is connected with the blood pump via the selector device. When the flow rate detected by the flow sensor decreases and the pressure detected by the pressure detector gets out of a normal range of pressures, the electrical control unit causes the selector device to disconnect the first pressure pulse generator from the blood pump and to connect the second pressure pulse generator with the blood pump.

4 Claims, 8 Drawing Sheets

P.P.S.-POSITIVE PRESSURE SOURCE
N.P.S.-NEGATIVE PRESSURE SOURCE

| FLAG | | CONTENTS |
|---|---|---|
| USED FOR THE APPARATUS ASSISTING THE LEFT HEART | LP | PRESENT PRESSURE VALUE |
| | LBFMMM | AVERAGE OF BLOOD FLOW RATE |
| | LBFMS | SET LOWER LIMIT OF AVERAGE BLOOD FLOW RATE |
| | LNPS | SET NEGATIVE PRESSURE |
| | LPPS | SET POSITIVE PRESSURE |
| | LAP2 | PRESSURE OBTAINED WHEN MEASUREMENT IS CHECKED |
| USED FOR THE APPARATUS ASSISTING THE RIGHT HEART | RP | PRESENT PRESSURE VALUE |
| | RBFMMM | AVERAGE OF BLOOD FLOW RATE |
| | RBFMS | SET LOWER LIMIT OF AVERAGE BLOOD FLOW RATE |
| | RNPS | SET NEGATIVE PRESSURE |
| | RPPS | SET POSITIVE PRESSURE |
| | RAP2 | PRESSURE OBTAINED WHEN MEASUREMENT IS CHECKED |
| B LA | | FLAG USED TO MAKE A DECISION AS TO WHETHER THE BLOOD FLOW RATE IS ABNORMAL. |
| PAA | | FLAG USED TO MAKE A DECISION AS TO WHETHER THE PRESSURE IS ABNORMAL. |

P.P.S.=POSITIVE PRESSURE SOURCE
N.P.S.=NEGATIVE PRESSURE SOURCE

APPARATUS FOR DRIVING BLOOD PUMP

FIELD OF THE INVENTION

The present invention relates to an apparatus for driving a blood pump such as a prefectly artificial heart, auxiliary artifical heart, or balloon pump by means of pressure pulses.

BACKGROUND OF THE INVENTION

A blood pump assists the action of the heart of a patient whose circulatory system has failed. Therefore, if the function of the apparatus driving the blood pump stops, the patient will be adversely affected. If a perfectly artificial heart fails, then the function of the heart is completely lost. If an auxillary artificial heart or a balloon pump fails, burden is suddenly imposed on the patient's weakened heart.

Accordingly, the frequency of troubles in blood pumps and driving apparatuses must be reduced. To cope with troubles in driving apparatuses, various means have been proposed. An apparatus disclosed in Japanese Patent Laid-Open No. 136,352/1983 incorporates a battery and a pressure tank to make preparations for disconnection from an external power supply. An apparatus disclosed in Japanese Patent Laid-Open No. 207,668/1985 is equipped with a plurality of pressure sensors to monitor the waveform of pressure. In the techniques disclosed in Japanese Patent Laid-Open Nos. 169,463/1983 and 249,655/1987, two preessure-generating devices are mounted. If one of them fails, it can be switched to the other.

The prior art method of detecting trouble in a driving apparatus consists in detecting the output pressure, comparing the detected pressure with a preset pressure, and regarding the apparatus as defective if there is a great difference between them. For example, in the techniques desclosed in Japanese Patent Laid-Open No. 249,655/1987, the period of pressure pulses and the level of pressure are checked.

The output pressure from a driving apparatus varies, depending on the resistance of the pipeline between the driving apparatus and a blood pump, on the characteristics of the apparatus, and on the condition of the patient's circulatory system, such as the blood pressure or a cardiogram. Therefore, when the detected pressure is compared with a preset value, it is necessary to give a tolerence to the preset value. For this reason, it is impossible to accurately detect abnormal pressure. In the worst case, a driving apparatus operating normally is judged to be defective.

SUMMARY OF THE INVENTION

It is an object of the present invention to provide an apparatus which drives a blood pump and which, if it is at fault, permits the fault to be accurately detected.

The above object is achieved by a driving apparatus comprising: a pressure pulse generator for producing pressure pulses; a pressure-detecting means for detecting the pressure generated by the pressure pulse generator; a flow-detecting means for measuring the flow rate of blood passing through a blood pump; and an abnormality-detecting means which, if the flow rate detected by the flow-detecting means drops and if the pressure detected by the pressure-detecting means comes out of a normal range of pressures, produces a signal indicating abnormality.

In this apparatus, if the flow rate of blood passing through the blood pump drops, and if the output pressure from a medical pump comes out of its normal pressure range, then the signal indicating abnormality is produced.

Other objects and features of the invention will appear in the course of the description thereof which follows.

DETAILED DESCRIPTION OF THE INVENTION

Figure 1:
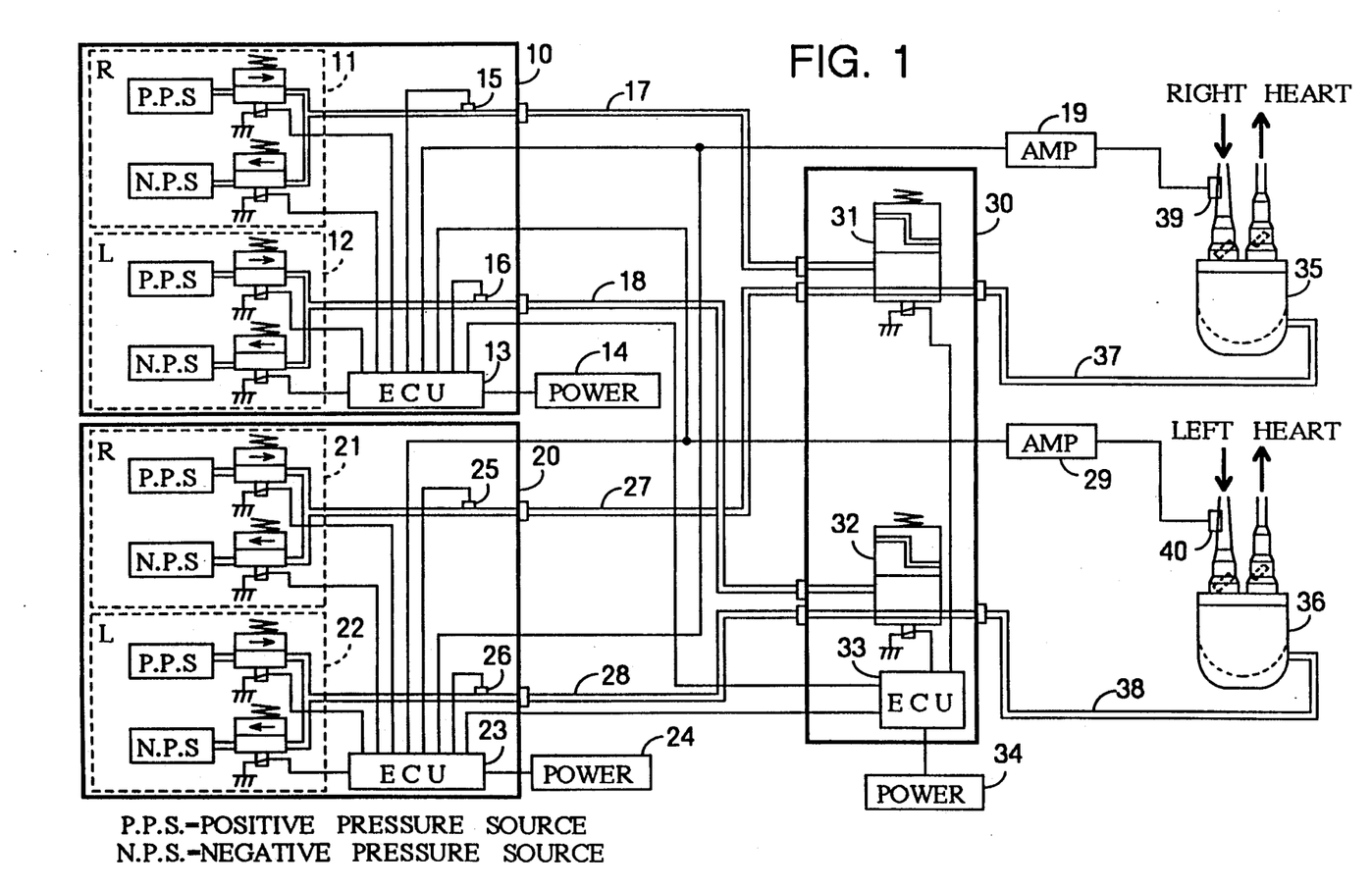
FIG. 1 is a circuit diagram of an apparatus according to the invention.

Referring to FIG. 1, there is shown a first example of the invention. A first blood pump-driving apparatus 10 comprises a pressure pulse generator 11 for producing pressure pulses for the right heart, another pressure pulse generator 12 for producing pressure pulses for the left heart, an electrical control unit (ECU) 13 for controlling the pulse generators 11 and 12, a power supply 14 for the electrical control unit 13, a pressure detector 15 for detecting the pressure produced by the pulse generator 11, and a pressure detector 16 for detecting the pressure produced by the pressure generator 12. The electrical control unit 13 controls the two pulse generators 11 and 12 according to information, such as blood pressure and a cardiogram, about an organism (not shown) in which a blood pump (not shown) has been infixed. The ECU 13 synchronizes the pressure pulses with the pulsation of the organism and controls the pressure according to the condition of the organism. The output pulses from the pulse generator 11 for the right heart are sent to the blood pump via a pipe 17 for the right heart. The output pulses from the pulse generator 12 for the left heart is sent to the blood pump throught a pipe 18 for the left heart. Since this blood pump-driving apparatus is similar in structure to the artificial heart-driving apparatus disclosed in Japanese Patent Laid-Open No. 169,460/1983, for the method of producing pressure pulses refer to this Japanese patent bulletin. The pipes 17 and 18 are connected with a selector device 30.

In the first example, a second blood-pump apparatus 20 that is identical in construction with the first blood pump-driving apparatus 10 is disposed. The second driving apparatus 20 includes a pressure pulse generator 21 for the right heart. The output of the pulse generator 21 is connected with the selector device 30 via a pipe 27 for the right heart. The second driving apparatus 20 further includes a pressure pulse generator 22 for producing pressure pulses. The output of the pulse generator 22 is connected with the selector device 30 via a pipe 28 for the left heart.

Selector valves 31 and 32 for the right heart and the left heart, respectively, and electrical control unit (ECU) 33, and a power supply 34 are disposed inside the selector device 30. The selector valve 31 that is a three-way solenoid valve acts to connect either the pipe 17 or 27 with the pipe 37 according to an output signal from the ECU 33. Similarly, the selector valve 32 is a three-way solenoid valve and connects either the pipe 18 or 28 with the pipe 38.

The pipe 37 is connected with an artificial heart pump 35 that is a blood pump. The pump 35 is connected with the right atrium and with the pulmonary artery via cannulas. When the pressure inside the pipe 37 increases, the artificial heart pump forces blood into the pulmonary artery. When the pressure decreases, the pump draws blood from the right atrium. Similarly, the pipe 38 is connected with an artificial heart pump 36 that is a blood pump. The pump 36 is connected with the left atrium and also with the main artery via cannulas. When the pressure inside the pipe 38 increases, the artificial heart pump forces blood into the main artery. When the pressure decreases, the pump takes in blood from the left atrium.

Since the selector device 30 connects the pipe 37 to the pipe 17 or 27, pressure pulses are fed into the artificial heart pump 35 to operate it. The selector device 30 connects the pipe 38 to the pipe 18 or 28, so that pressures pulses are fed into the artificial heart pump 36 to operate it.

A blood flow sensor 39 that is a flow-detecting means for detecting the flow rate for blood is disposed either in the artificial heart pump 35 or in the cannula extending between the pump 35 and the organism. The sensor 39 measures the flow rate of the blood passing through the pump 35. The output signal from the sensor 39 is supplied via an amplifier 19 to the ECU 13 in the first blood pump-driving apparatus 10 and to the ECU 23 in the second blood pump-driving apparatus 20. Likewise, a blood sensor 40 that is a flow-detecting means for detecting the flow rate of blood is placed either in the artificial heart pump 36 or in the cannula extending between the pump 36 and the organism. The output signal from the sensor 40 is furnished via an amplifier 29 to the ECU 13 in the first driving apparatus 10 and to the ECU 23 in the second driving apparatus 20.

Figure 2:
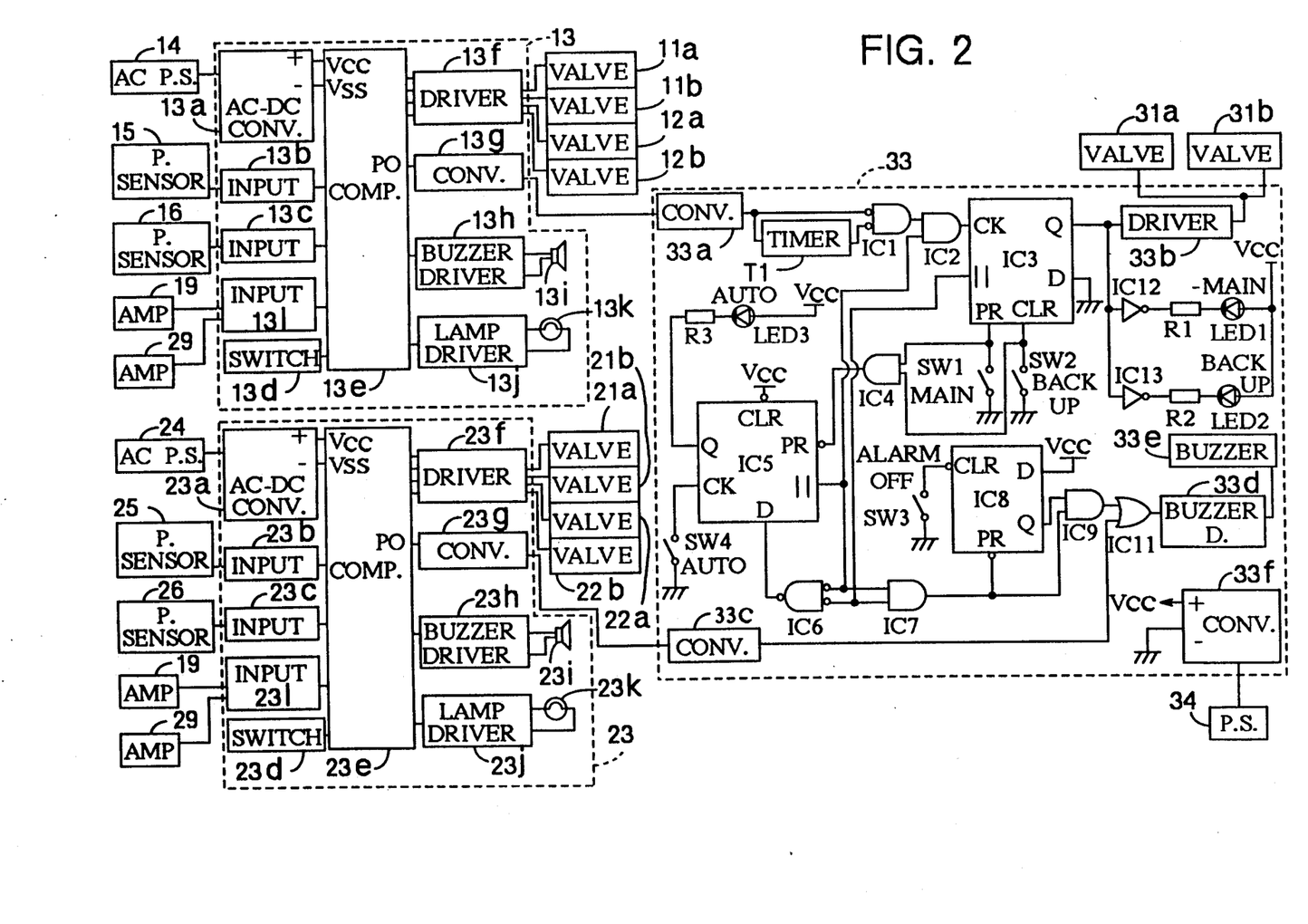
FIG. 2 is a circuit diagram of the electrical control units 13, 23, 33 shown in FIG. 1.

The circuit configuration of the ECUs 13, 23, 33 are next described by referring to FIG. 2. The ECU 13 incorporates a microcomputer 13e in the form of one chip. The microcomputer 13e includes a read-only memory (ROM) and a random access memory (RAM). An AC voltage produced by the AC power supply 14 is converted into a DC voltage by an AC-DC converter 13a and applied to the microcomputer 13e. The output signals from the pressure detectors 15 and 16 are sent to the microcomputer 13e via input circuits 13b and 13c, respectively. The output signals from the amplifiers 19 and 29 are fed to the microcomputer 13e via an input circuit 131. The microcomputer 13e supplies a signal to a driver 13f, which then actuates four solenoid valves 11a, 11b, 12a, 12b. The solenoid valves 11a and 11b are located inside the pressure pulse generator 11 and make a switch between a positive pressure and a negative pressure for the right heart. The solenoid valves 12a and 12b are positioned inside the pressure pulse generator 12 and make a switch between a positive pressure and a negative pressure for the left heart. An electro-optical converter 13g converts the electrical signal produced by the microcomputer 13e into an optical signal which is sent to the ECU 33 via an optical fiber. A buzzer driver 13h and a lamp driver 13j receive signals from the microcomputer 13e and drive a buzzer 13i and a lamp 13k, respectively. The ECU 23 has the same circuit configuration as the ECU 13.

The ECU 33 has four switches SW1-SW4 and three flip-flops IC3, IC5, IC8. The switch SW1 is used to select the first pressure pulse generator that is the main pressure pulse generator. When the switch SW1 is closed, the flip-flop IC3 is present. Then, the Q terminal of this flip-flop goes high. At this time, the driver 33b actuates the solenoid valves 31a and 31b which actuate the selector valves 31 and 32, respectively, in the selector device 30 to connect the pipes 17 and 18 with the pipes 37 and 38, respectively. Also, the driver 33b lights up a light-emitting diode LED1 and causes another light-emitting diode LED2 to go out. LED1 illuminates the word "MAIN" when the diode lights up. LED2 illuminates the idiom "BACK UP" when the diode lights up.

The switch SW2 is employed to select the second pressure pulse generator that backs up the first pressure pulse generator. When the switch SW2 is closed, the flip-flop IC3 is reset to cause its Q terminal to go high. Under this condition, the driver 33b activates the solenoid valves 31a and 31b which activate the selector valves 31 and 32, respectively, in the selector device 30 to connect the piper 27 and 28 with the pipes 37 and 38, respectively. LED1 for illuminating the "MAIN" is caused to go out. LED2 for illuminating the idiom "BACK UP" is lit up.

For the flip-flop IC3, priority is given to the resetting rather than presetting and, therefore, when the switches SW1 SW2 are simultaneously closed, the flip-flop selects the backup pressure pulse generator.

Since the voltage at the Q terminal of the flip-flop IC3 is normally at a high level, if both switches SW1 and SW2 are open, the main pressure pulse generator is selected.

The switch SW4 is used to permit the selected pressure pulse generator to be automatically switched from the main pulse generator to the backup pulse generator. When the main pulse generator is selected, the $\overline{Q}$ terminal of the flip-flop IC3 is at a low level. When the switches SW1 and SW2 are open, a flip-flop IC4 causes the present terminal of the flip-flop IC5 to go high. Also, the reset terminal is at a high level. If no signal is applied to the clock terminal after the power is turned on, the Q terminal of the flip-flop IC5 is at a high level, while the $\overline{Q}$ terminal is at a low level. Therefore, one input terminal of the flip-flop IC2 hoes low to inhibit the output signal from the ECU 13 from being applied to the CK terminal of the flip-flop IC3. At this time, the output from the flip-flop IC6 goes low. When the switch SW4 is opened, clock pulses are applied to the flip-flop IC5, so that the Q terminal of the flip-flop IC5 goes low, while the $\overline{Q}$ terminal goes high. As a result, a light-emitting diode LED3 for illuminating the word "AUTO" lights up. One input terminal of the flip-flop IC2 goes high and so the signal applied to the other input terminal of the flip-flop IC2 appears at the output terminal as it is.

The optical signal from the electro-optical converter of the ECU 13 is applied to an opto-electrical converter included in the ECU 33, whereby the optical signal is converted into an electrical signal. A timer T2 and a flip-flop IC1 form a low-pass filter which cuts off RF signals. If the ECU 13 delivers a high-level signal for a long period, the output from the flip-flop IC1 goes high. Then, the CK terminal of the flip-flop IC 13 goes high. Since the voltage at the D terminal of the flip-flop IC3 is kept low, the Q terminal of the flip-flop IC3 goes low. Accordingly, the driver 33b causes the selector device 30 to connect the backup, second pressure pulse generator with the blood pump. At the same time, LED1 for illuminating the word "MAIN" is made to go out. LED 2 for illuminating the idiom "BACK UP" is lit up. In this way, when both switches SW1 and SW2 are open, if the switch SW3 is depressed once, the pressure pulse generator is automatically switched to the other by the selector device after the high-level signal from the ECU 13 persists for a long time.

If the switch SW4 is depressed once to permit the pressure pulse gernerator to be automatically switched to the other as described above, the $\bar{Q}$ terminal of the filp-flop IC5 goes high, causing the Q terminal of the flip-flop IC5 to go high. Then, the output of the flip-flop IC6 goes high. If the switch SW4 is again opened, the $\bar{Q}$ terminal of the flip-flop IC5 again goes low. This prevents the output signal from the ECU 13 from being applied to the CK terminal of the flip-flop IC3, so that the pulse generator can no longer be switched to the other.

When either the switch SW1 or the switch SW2 is opened, the output of the flip-flop IC4 goes low to preset the flip-flop IC5. Then, the $\bar{Q}$ terminal goes low, and the pressure pulse generator is no longer automatically switched to the other.

When the used pressure pulse generator is allowed to be automatically selected, the $\bar{Q}$ terminal of the flip-flop IC5 goes high the switch the used pulse generator to the other pulse generator automaticlly. At the same time, the $\bar{Q}$ terminal of the flip-flop IC3 goes high. At this time, the output of the flip-flop IC7 goes high. If the switch SW3 for causing an alarm to stop is open, the Q terminal geos high, because a flip-flop IC8 has been present. Then, a flip-flop IC11 produces a high-level signal. At this time, a buzzer driver 33d causes a buzzer 33e to sound. If the switch SW3 is open, a flip-flop IC8 is reset, making the Q terminal of the flip-flop IC3 go low. In this state, the buzzer is not allowed to sound. The buzzer 33e also sounds when the output from the electro-optical converter 23g of the ECU 23 is high. The output voltage from the AC power supply 34 is converted by an AC-DC converter 33f into a DC voltage that drives the circuit of the ECU 33.

Figure 3:
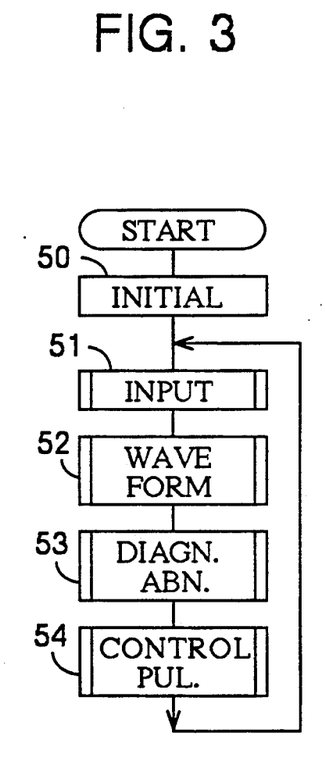
FIG. 3 is a flowchart illustrating the main routine executed by the electrical control unit 13 or 23 shown in FIG. 1.

The microcomputers 13e and 23e shown in FIG. 2 operate in the manner as illustrated in the flowcharts of FIGS. 1-8. FIG. 3 illustrates the main routine executed by the microcomputers. When each microcomputer is started, its internal memory, input and output terminals are initialized (step 50). Then, a signal input routine (step 51), a waveform display routine (step 52), an abnormality diagnostic routine (step 53), and a pulsation control routine (step 54) are repeated.

In the signal input routine, pressure signals from the pressure detectors 15, 16, 25, 26 and flow signals from the amplifiers 19 and 29 are applied to the microcomputer, which then calculates average values or performs other arithmetic operations. When switches 13d and 23d are operated to set a flow rate and a pressure value, respectively, these values are input to the microcomputer also in this routine. The output value from the pressure detector 15 or 25 or the pressure pulse generator for assisting the left heart is indicated by LP. The output value from the pressure detector 16 or 26 of the pressure pulse generator for assisting the right heart is indicated by RP. The average of the flow rate of blood flowing through the left heart is indicated by LBFMMM. The average of the flow rate of blood passing through the right heart is indicated by RBFMMM. The set lower limit of the average blood flow rate through the left heart is indicated by LBFMS. The set lower limit of the average blood flow rate through the right heart is indicated by RBFMS.

In the waveform display routine, various measured values are processed to display waveforms and data on a display device (not shown).

In the abnormality diagnostic routine, a check is performed, using measured flow rates and pressure values, to see whether the pressure pulse generator is at fault. If it is at fault, the microcomputer sends an abnormality signal to the selector device 30.

In the pulsation control routine, the solenoid valves in the pressure pulse generator are activated according to a signal representing a cardiogram obtained from the organism, in a manner not illustrated, to swich the pressure to a different value.

Figure 4:
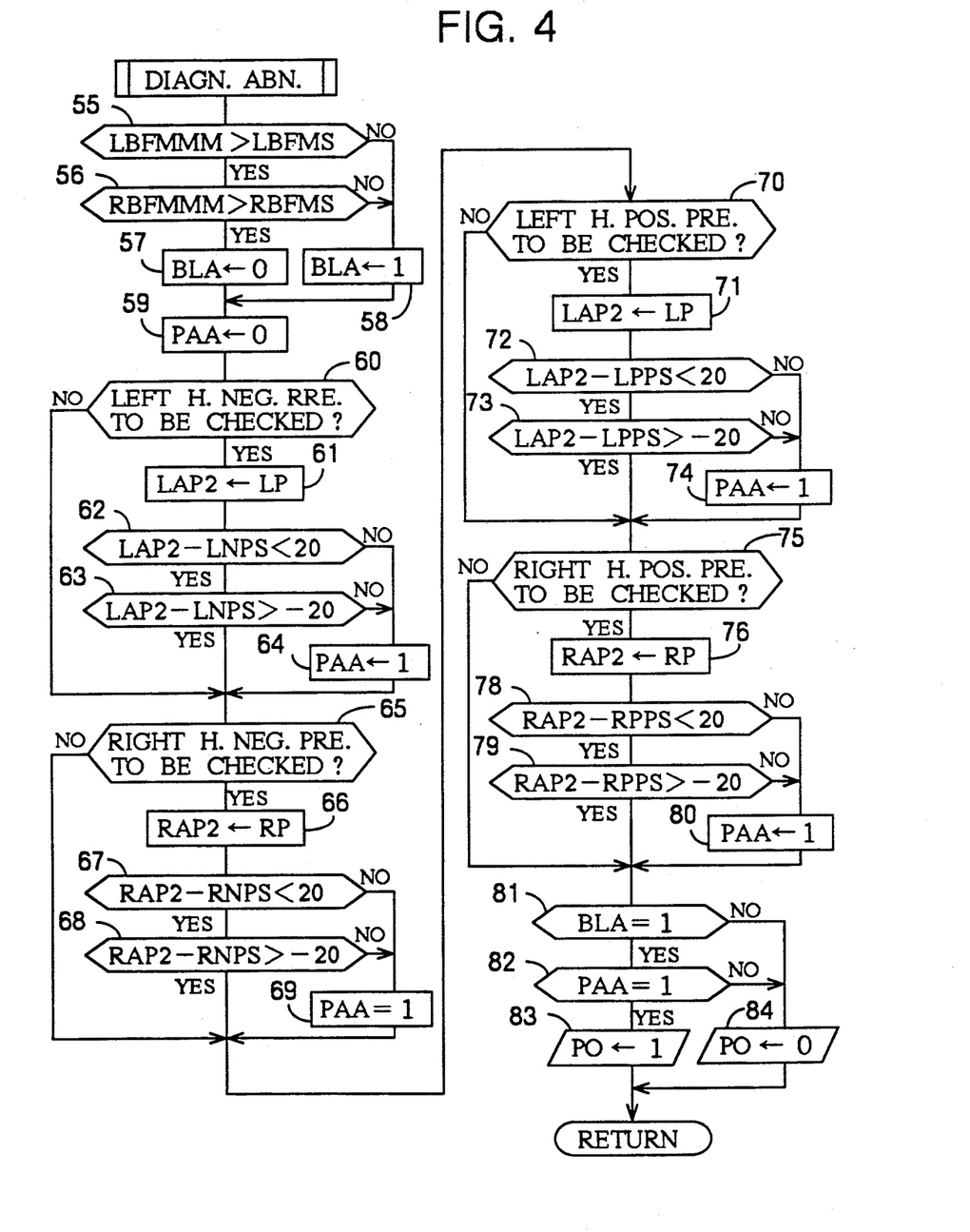
FIG. 4 is a flowchart illustrating the abnormality diagnostic routine illustrated in FIG. 3.
Figure 5:
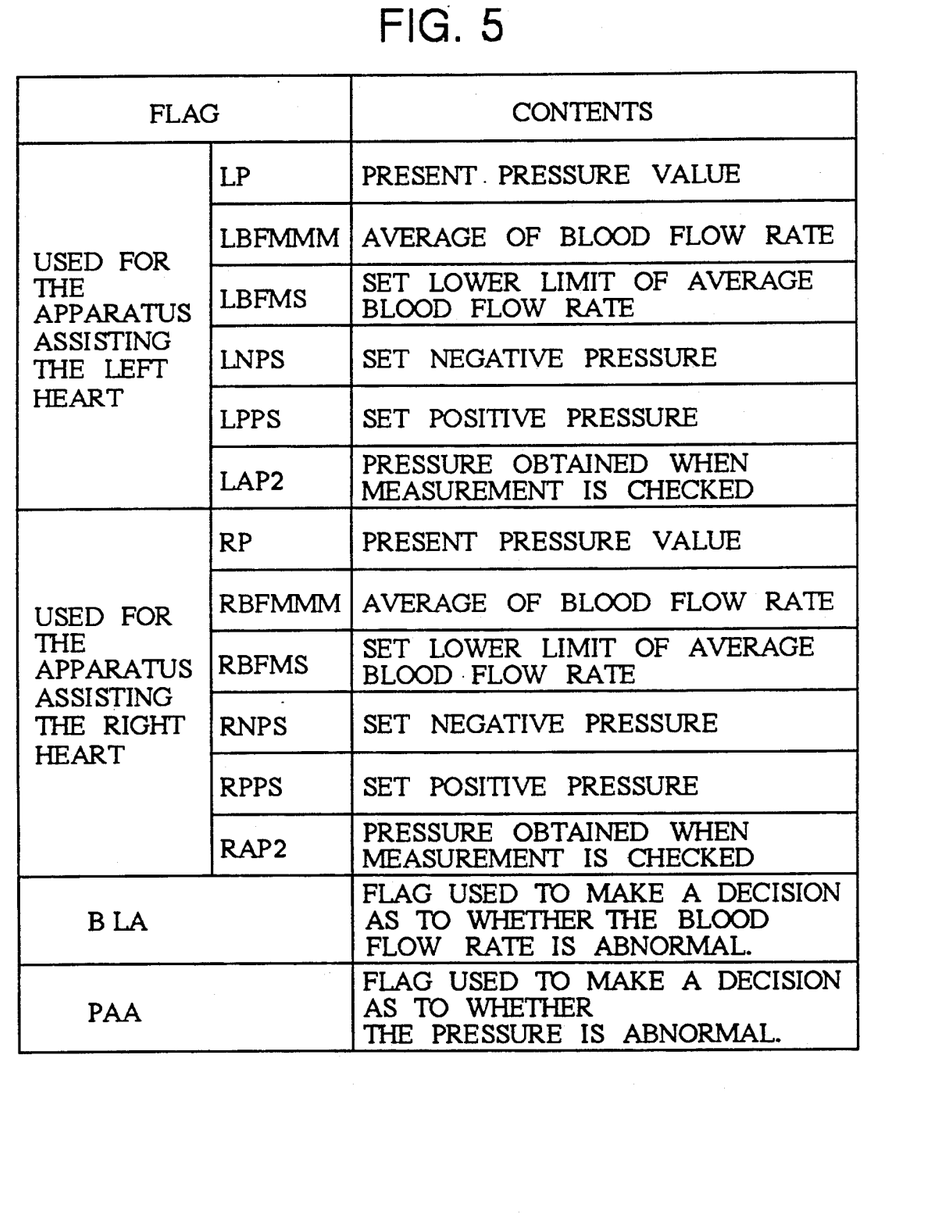
FIG. 5 is a table illustrating the flags used in the flowchart of FIG. 4.

The abnormality diagnostic routine is next described in detail by referring to FIG. 4. The contents of flags used in this routine are shown in FIG. 5.

When the abnormality diagnostic routine is executed, the flow rates of blood delivered from the blood pumps are checked (steps 55-58). If the average blood flow rate LBFMMM delivered from the blood pump for the left heart is less than the set lower limit LBFMS of the average blood flow rate through the left heart, then a flag BLA indicating whether the blood flow rate is abnormal is set to 1. If the average blood flow rate RBFMMM delivered from the blood pump for the right heart is less than the set lower limit RBFMS of of the average blood flow rate through the right heart, then the flag BLA is set to 1. In the other cases, the flag BLA is set to 0. Accordingly, when the flow rate of blood is less than the set value, the flow rate is regarded as abnormal.

Figure 6:
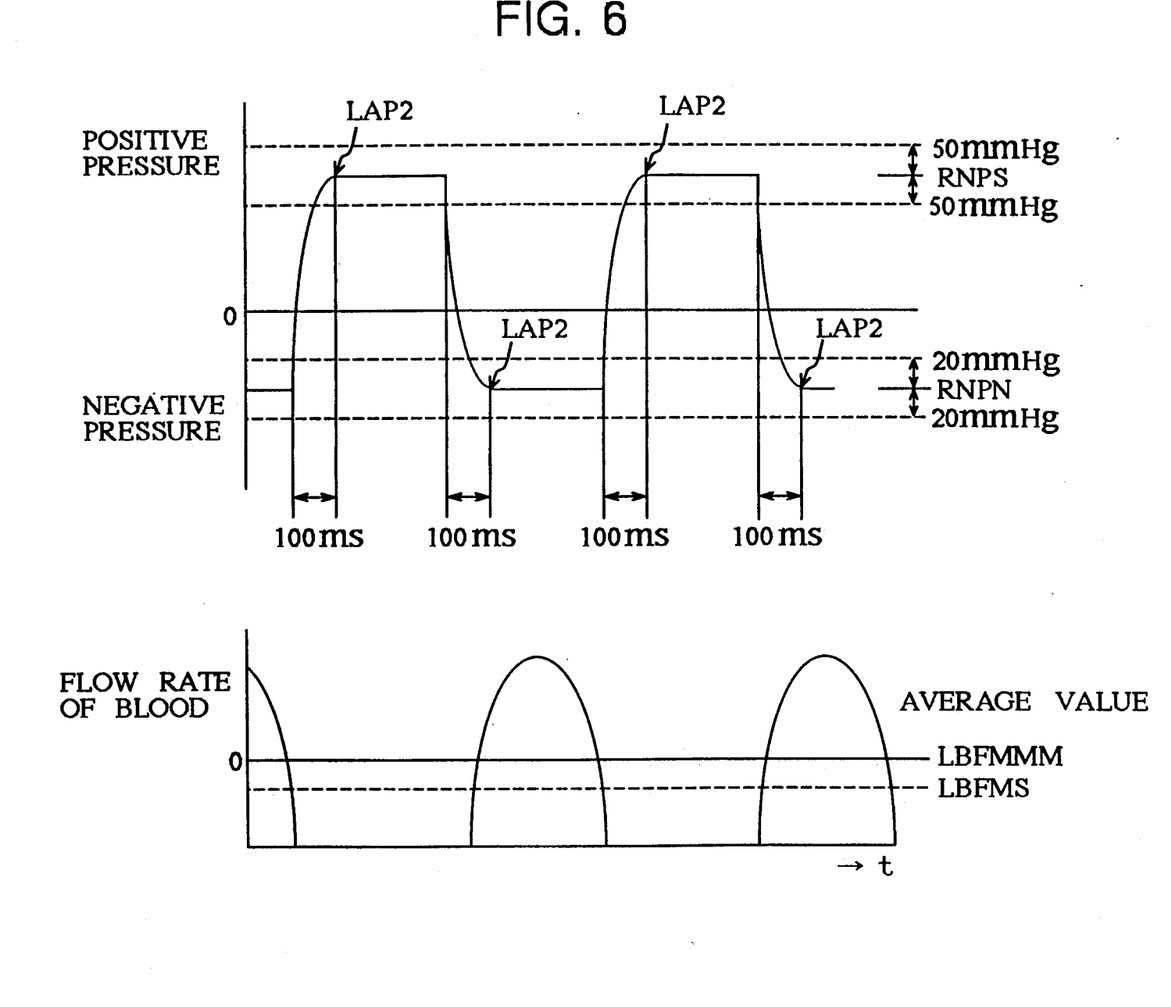
FIG. 6 is a graph for illustrating the operation of the apparatus shown in FIG. 1.

Subsequently, the values of pressure supplied to the blood pumps are checked (steps 59-80). First, a flag PAA indicating abnormal pressure is set to 0. If it is the time to check the positive pressure or the negative pressure for the left or right heart, the pressure is diagnosed. The checking time is determined by the minimum possible period of the pressure pulses. As an example, if the possible time for which a positive pressure is applied is 100 ms, then the check is done at any arbitrary time within 100 msec after the pressure is switched from a negative pressure to a positive pressure. In the present example, as shown in FIG. 6, the positive pressure is checked when 100 ms elapses since the application of the positive pressure, and the negative pressure is checked when 100 ms passes since the application of the negative pressure. When the negative pressure for the left heart is diagnosed, if any one of relations (1) and (2) described below is not satisfied, then the flag PAA for indicating abnormal pressure is set to 1.

$$LAP2 - LNPS < 20 \text{ mmHg} \tag{1}$$

$$LAP2 - LNPS > -20 \text{ mmHg} \tag{2}$$

When the negative pressure for the right heart is diagnosed, if any one of relations (3) and (4) below is not fulfilled, then the flag PAA is set to 1.

$$RAP2-RNPS < 20 \text{ mmHg} \quad (3)$$

$$RAP2-RNPS > -20 \text{ mmHg} \quad (4)$$

The formulas (1)–(4) include the term "20 mmHg" to take account of variations occurring in the apparatus.

When the positive pressure for the left heart is diagnosed, if any one of relations (5) and (6) below is not catered for, then the flag PAA indicating abnormal pressure is set to 1.

$$LAP2-LPPS < 20 \text{ mmHg} \quad (5)$$

$$LAP2-LPPS > -20 \text{ mmHg} \quad (6)$$

When the positive pressure for the right heart is diagnosed, if any one of relations (7) and (8) below is not fulfilled, then the flag PAA is set to 1.

$$RAP2-RPPS < 20 \text{ mmHg} \quad (7)$$

$$RAP2-RPPS > -20 \text{ mmHg} \quad (8)$$

The formulas (5)–(8) include the term "50 mmHg" to take account of variations occurring in the apparatus.

Therefore, if the positive and negative pressures for both hearts are normal, then the flag PAA is 0. If any one of them is abnormal, then the flag PAA is set to 1. In this example, if any one of the positive pressure for the left heart, the negative pressure for the left heart, the positive pressure for the right heart, and the negative pressure for the right heart becomes abnormal once, the flag PAA for indicating abnormal pressure is set to 1. In order to make the decision more accurate, if any one of them remains abnormal while more than 5 pulses are beaten, then the flag PAA may be set to 1.

If both flag BLA indicating abnormal blood flow and the flag PAA indicating abnormal pressure assume the value of 1, then a port PO is set to 1, i.e., goes high. If any one of them is 0, the port PO is set to 0, i.e., goes low. That is, only when the flow rate of blood decreases and the pressure gets out of the tolerable range, a high-level signal is transmitted to the ECU 33. When the ECU 13 sends a high-level signal to the ECU 33, the ECU 33 causes the selector device 30 to connect the blood pumps 35, 36 with the second blood pump-driving device 20 as described above. Therefore, if the pressure pulse generator in the first blood pump-driving device 10 is at fault, the system can still be controlled without stopping the pumps.

In this example, the first driving apparatus 10 and the second driving apparatus 20 are identical in structure. Since the second apparatus 20 is used only when the first apparatus 10 is at fault, the secnd apparatus can have only the indispensable functions. Thus, the total cost can be curtailed by using a simple and economical apparatus as the second blood pump-driving apparatus.

Figure 7:
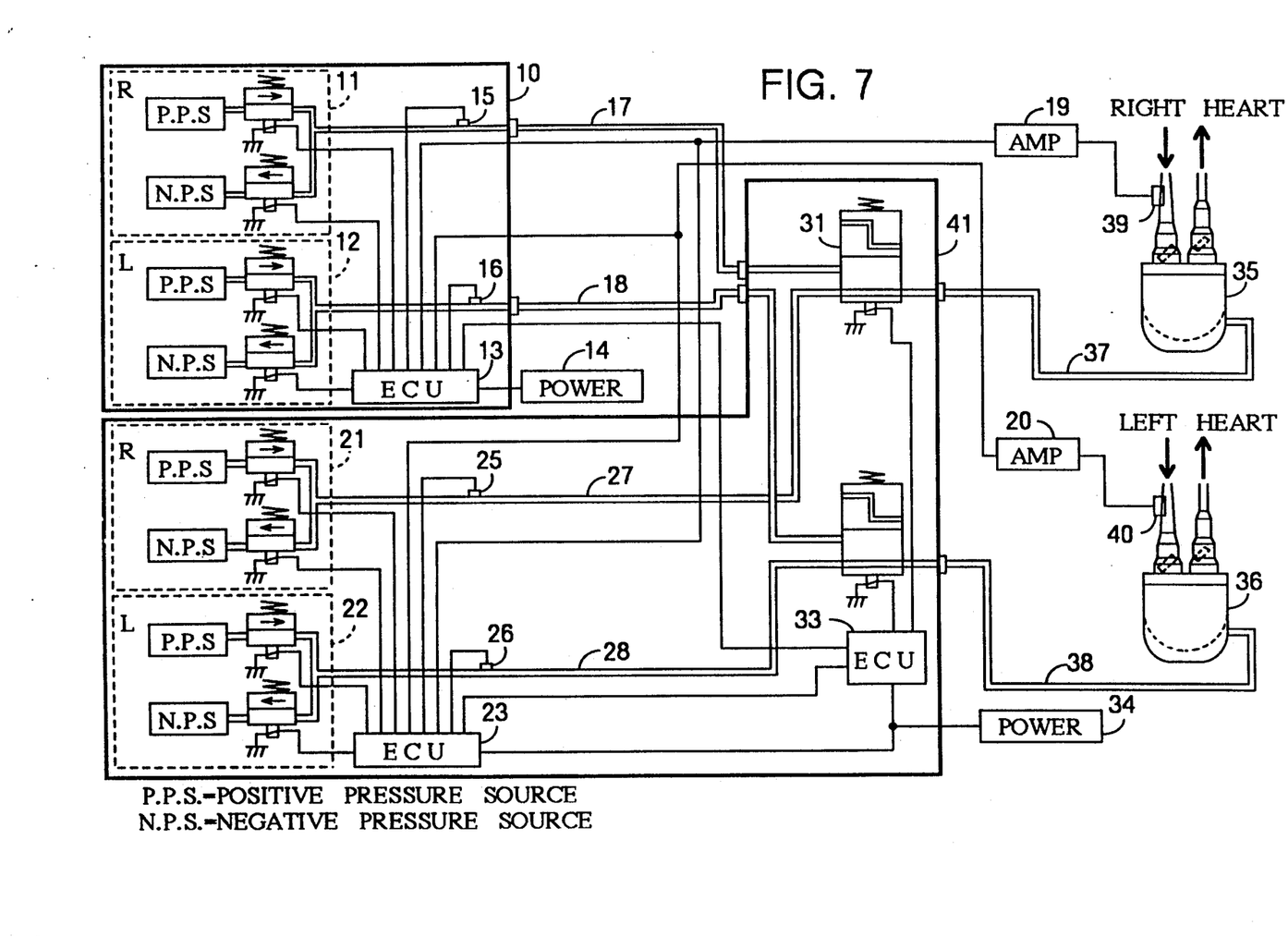
FIGS. 7 and 8 are circuit diagrams of other apparatuses according to the invention.
Figure 8:
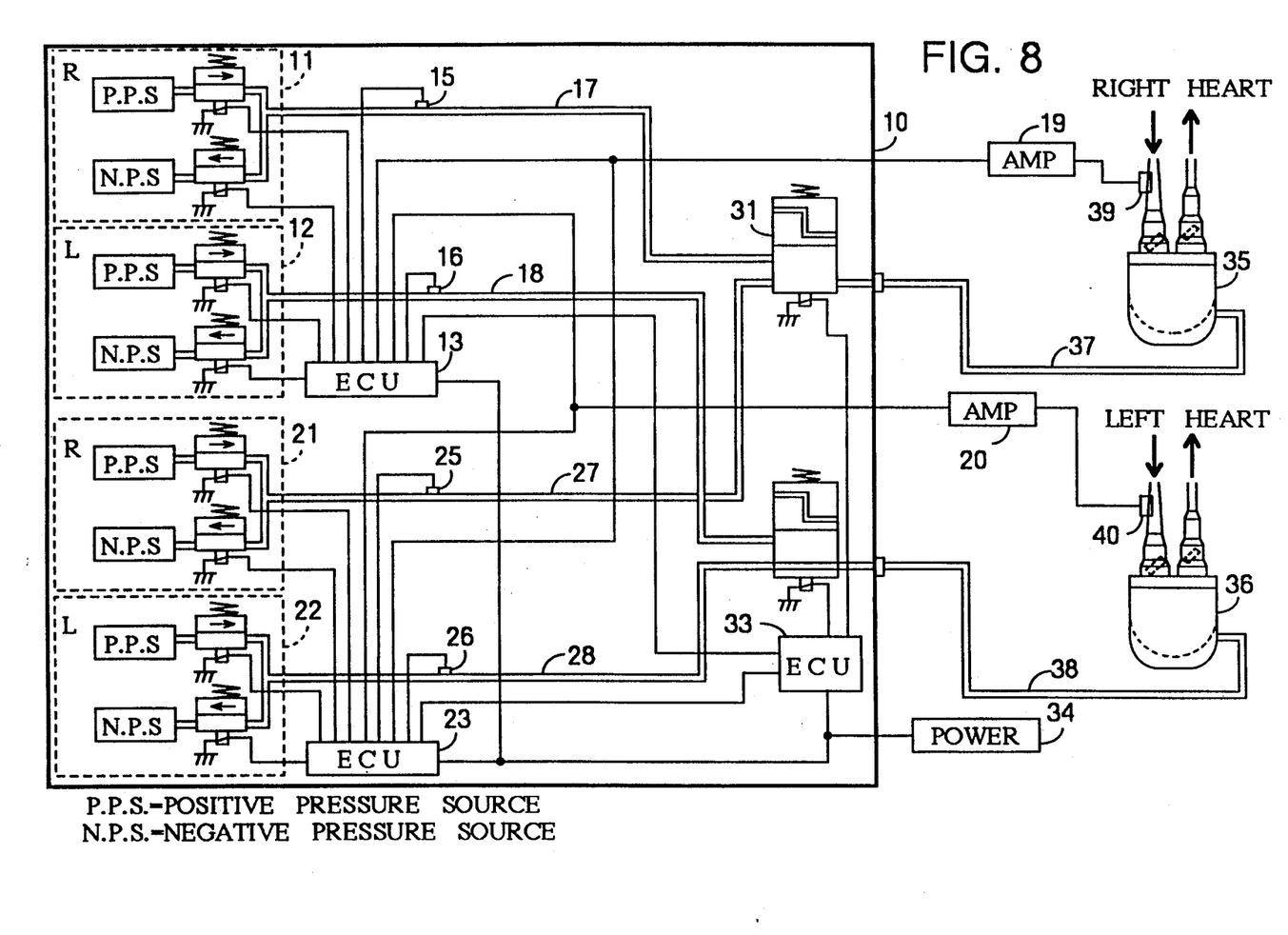

Another example of the invention is shown in FIG. 7, where the second blood pump-driving apparatus and a selector device are combined into a backup apparatus 41. This reduces the number of apparatuses and devices and facilitates wiring among the apparatuses and devices. It is to be noted that like components are denoted by like reference numerals in all the figures including FIG. 7. A further example of the invention is shown in FIG. 8, where the first blood pump-driving apparatus, the second blood pump-driving apparatus, and the selector device are combined into a unit.

As described thus far, in accordance with the present invention, the system is regarded as defective when not only a pressure decrease but a blood flow rate decrease is detected. Consequently, the decision is made more precisely than cases where the decision is made, based on only the blood flow rates or on the pressures.

Where abnormality is detected using only the blood flow rates, the pressure pulse generator may be switched to the other even when a hose extending between a driving apparatus and a blood pump is bent or when a flow-detecting means is at fault. In these cases, the heretofore used pressure pulse generator itself is not at fault. If the pressure pulse generator is switched to the other, the trouble in the hose or in the flow-detecting means is not remedied and so the changeover of the pressure pulse generator produces no fruitful results. When blood is not sent back from the organism as encountered when a large amount of blood is lost due to profuse bleeding, the pressure pulse generator is not at fault and, therefore, it is not desired to switch the apparatus to the other.

Where abnormality is detected using only the pressure values, if the pressure is abnormal but the flow rates of blood flowing through the blood pumps are normal, then it is not necessary to switch the pressure pulse generator to the other.

In this way, when the pressure pulse generator is switched to the other when abnormality occurs, the following two requirements must be met: (1) Whenever the used generator should be switched to the other, the switching operation is performed; (2) When the used generator is not required to be switched to the other, no switching operation is carried out. If the pressure pulse generator is switched to the other when only abnormal pressure or abnormal blood flow rate is detected, then these requirements are not satisfied. On the other hand, where the pressure pulse generator is switched to the other when both a blood flow decrease and abnormal pressure are detected, the requirements are fulfilled more strictly. In this manner, the apparatus which switches the pressure pulse generator to the other when abnormality occurs is caused to detect the abnormality, using the blood flow rates and the pressures. This yields greater advantages.

A control means which detects abnormality and switches the pressure pulse generator to the other is composed of an abnormality-detecting means incorporated in a first pressure pulse generator and a selector control means. This permits the selector control means to be disposed apart from the first pressure generator. The abnormality-detecting means produces a signal indicating abnormality when the flow rate detected by a flow-detecting means decreases and, at the same time, the pressure detected by a pressure-detecting means decreases. When the signal indicating abnormality is being produced by the abnormality-detecting means, the selector control means causes the selector means to connect a second pressure pulse generator with the blood pump. Since th first pressure pulse generator and the selector control means are separated from each other, it is necessary to send information indicating the normal range of pressures porduced by the first pressure pulse generator to the control means. If the abnormality-detecting portion of the control means is included in the first pressure pulse generator, it is only necessary to transmit a two-valued signal indicating whether the portion between the first pressure pulse generator and the selector control means is at fault or not. Hence, the reliability of the communication is enhanced. In the present example, the second pressure pulse generator, the selector control means, and the selector means are combined into a backup apparatus which operates when abnormality occurs. It enables the normal blood pump to be controlled by using the first pressure pulse generator. Since the backup apparatus is added, a further function is added which serves when abnormality takes place. Accordingly, the backup apparatus is used differently according to the condition of the patient, which is a convenience. In this case, the first pressure generator is preferably capable of coping with abnormality such as when the patient's condition takes a sudden turn for the worse or when the pressure pulse generator has a light trouble. However, it is only necessary that the second pressure pulse generator in the backup apparatus can provide general control and so the backup apparatus can be fabricated economically.

What is claimed is:

1. An apparatus for driving a blood pump, comprising:
    a pressure pulse generator for producing pressure pulses;
    a pressure-detecting means for detecting the pressure produced by the pressure pulse generator;
    a flow-detecting means for measuring the flow rate of blood passing through the blood pump; and
    an abnormality-detecting means which produces a signal indicating abnormality or fault when the flow rate detected by the flow-detecting means decreases to an abnormal flow rate and, at the same time, the pressure detected by the pressure-detecting means gets out of a normal range of pressures.

2. An apparatus for driving a blood pump, comprising:
    a first pressure pulse generator for producing pressure pulses;
    a second pressure pulse generator for producing pressure pulses;
    a pressure-detecting means for detecting the pressure produced by the first pressure pulse generator;
    a flow-detecting means for measuring the flow rate of blood passing through the blood pump;
    a selector means connected among the first pressure pulse generator and the second pressure pulse generator, so as to connect the first pressure pulse generator with the blood pump and disconnect the second pressure pulse generator from the blood pump; and
    a control means which, when the flow rate detected by the flow-detecting means decreases and the pressure detected by the pressure-detecting means gets out of a normal range of pressure, causes the selector means to disconnect the first pressure pulse generator from the blood pump and to connect the second pressure pulse generator with the blood pump.

3. An apparatus for driving a blood pump as set forth in claim 2, wherein said control means comprises: an abnormality-detecting means which is included in the first pressure pulse generator and which, when the flow rate detected by the flow-detecting means and the pressure detected by the pressure-detecting means decrease, produces a signal indicating abnormality; and a selector control means which, when the signal indicating abnormality is being produced by the abnormality-detecting means, causes the selector means to disconnect the first pressure pulse generator from the blood pump and to connect the second pressure pulse generator with the blood pump.

4. An apparatus for driving a blood pump as set forth in claim 2, wherein the second pulse generator and the selector means are unitary.

* * * * *